(12) United States Patent
Andersson et al.

(10) Patent No.: US 11,369,705 B2
(45) Date of Patent: Jun. 28, 2022

(54) LIGHT CONTROL SYSTEM AND A METHOD FOR EXPOSING A SUB-PORTION OF A SPACE WITH LIGHT WITHIN A PREDETERMINED SPECTRAL RANGE AT A PREDETERMINED THRESHOLD INTENSITY

(71) Applicant: BrainLit AB, Lund (SE)

(72) Inventors: Peter K Andersson, Skäret (SE); Tord Wingren, Malmö (SE)

(73) Assignee: BrainLit AB, Lund (SE)

( * ) Notice: Subject to any disclaimer, the term of this patent is extended or adjusted under 35 U.S.C. 154(b) by 0 days.

(21) Appl. No.: 16/329,374

(22) PCT Filed: Sep. 1, 2017

(86) PCT No.: PCT/EP2017/071939
§ 371 (c)(1),
(2) Date: Feb. 28, 2019

(87) PCT Pub. No.: WO2018/041986
PCT Pub. Date: Mar. 8, 2018

(65) Prior Publication Data
US 2019/0192710 A1    Jun. 27, 2019

(30) Foreign Application Priority Data
Sep. 2, 2016   (EP) .................................... 16187071

(51) Int. Cl.
*A61L 2/10*   (2006.01)
*A61L 9/20*   (2006.01)
(Continued)

(52) U.S. Cl.
CPC ................... *A61L 2/10* (2013.01); *A61L 9/20* (2013.01); *A61M 21/00* (2013.01); *H05B 47/11* (2020.01);
(Continued)

(58) Field of Classification Search
CPC . A61L 2/208; A61L 2/202; A61L 2/10; A61L 9/20; A61L 2202/11;
(Continued)

(56) References Cited

U.S. PATENT DOCUMENTS 9,064,394 B1 *   6/2015   Trundle ................. H04N 7/188
9,681,510 B2 *   6/2017   van de Ven ............ H05B 45/00
(Continued)

FOREIGN PATENT DOCUMENTS

CN   102027807 A    4/2011
CN   202554523 U    11/2012
(Continued)

OTHER PUBLICATIONS

International Search Report and Written Opinion of PCT/EP2017/071939 dated Dec. 21, 2017, 22 pages.
(Continued)

*Primary Examiner* — Abdullah A Riyami
*Assistant Examiner* — Syed M Kaiser
(74) *Attorney, Agent, or Firm* — Brundidge & Stanger, P.C.

(57) ABSTRACT

The present invention relates to a light control system. The light control system comprising: a plurality of light sources each configured to emit light within a predetermined spectral range, each of the plurality of light sources being configured to illuminate a corresponding sub-portion of a space, a sensor configured to within the space, detect a location of a human or an animal; and a control engine configured to control the plurality of light sources based on the detected location of the human or the animal such that a sub-portion of the space in which the human or the animal is not present is exposed to the light within the predetermined spectral range at a predetermined threshold intensity. A method for exposing a sub-portion of a space with light within a
(Continued)

predetermined spectral range at a predetermined threshold intensity is also provided.

9 Claims, 4 Drawing Sheets

(51) Int. Cl.
  *H05B 47/16* (2020.01)
  *H05B 47/11* (2020.01)
  *A61M 21/00* (2006.01)
  *H05B 47/125* (2020.01)
  *H05B 47/115* (2020.01)

(52) U.S. Cl.
  CPC ........... *H05B 47/115* (2020.01); *H05B 47/16* (2020.01); *A61L 2202/11* (2013.01); *A61L 2202/14* (2013.01); *A61L 2202/25* (2013.01); *A61M 2021/0044* (2013.01); *A61M 2240/00* (2013.01); *H05B 47/125* (2020.01); *Y02B 20/40* (2013.01)

(58) Field of Classification Search
  CPC .... A61L 2202/14; A61M 21/00; H05B 47/16; H05B 47/105; A01K 1/00; A01K 13/001; A01K 43/05; A01K 51/08
  See application file for complete search history.

(56) References Cited

U.S. PATENT DOCUMENTS

| | | | | |
|---|---|---|---|---|
| 9,692,954 | B2* | 6/2017 | Delmonico | H04N 5/2256 |
| 9,826,597 | B2* | 11/2017 | Tran | H05B 45/37 |
| 10,335,572 | B1* | 7/2019 | Kumar | A61H 9/0078 |
| 2002/0033134 | A1* | 3/2002 | Fannon | F26B 3/28 |
| | | | | 118/667 |
| 2006/0188389 | A1* | 8/2006 | Levy | A61L 2/24 |
| | | | | 422/24 |
| 2007/0115665 | A1* | 5/2007 | Mueller | F21K 9/00 |
| | | | | 362/276 |
| 2008/0310850 | A1* | 12/2008 | Pederson | G07C 9/37 |
| | | | | 398/135 |
| 2009/0046152 | A1* | 2/2009 | Aman | G06K 9/3216 |
| | | | | 348/157 |
| 2011/0009163 | A1* | 1/2011 | Fletcher | G02B 21/0008 |
| | | | | 455/556.1 |
| 2011/0069960 | A1* | 3/2011 | Knapp | H04L 12/437 |
| | | | | 398/103 |
| 2011/0211110 | A1* | 9/2011 | Doublet | H05B 47/105 |
| | | | | 348/370 |
| 2012/0126134 | A1* | 5/2012 | Deal | A61L 9/20 |
| | | | | 250/372 |
| 2012/0199003 | A1* | 8/2012 | Melikov | A61L 9/20 |
| | | | | 95/273 |
| 2012/0206050 | A1* | 8/2012 | Spero | B60Q 1/1423 |
| | | | | 315/152 |
| 2012/0235579 | A1* | 9/2012 | Chemel | H05B 47/19 |
| | | | | 315/152 |
| 2013/0211481 | A1* | 8/2013 | Ward | A61N 5/0624 |
| | | | | 607/89 |
| 2013/0329068 | A1* | 12/2013 | Hamanaka | H04N 5/23206 |
| | | | | 348/218.1 |
| 2014/0334653 | A1* | 11/2014 | Luna | H05B 47/105 |
| | | | | 381/332 |
| 2014/0365018 | A1* | 12/2014 | Kusukame | H05B 47/19 |
| | | | | 700/276 |
| 2015/0035437 | A1* | 2/2015 | Panopoulos | H05B 47/19 |
| | | | | 315/112 |
| 2015/0061509 | A1* | 3/2015 | Karlicek | H05B 47/105 |
| | | | | 315/153 |
| 2015/0070319 | A1* | 3/2015 | Pryor | G06F 3/011 |
| | | | | 345/175 |
| 2015/0086420 | A1* | 3/2015 | Trapani | A61L 2/202 |
| | | | | 422/24 |
| 2015/0233962 | A1* | 8/2015 | Tchoryk | G01P 5/26 |
| | | | | 356/28.5 |
| 2015/0359070 | A1* | 12/2015 | Mead | H05B 47/16 |
| | | | | 315/154 |
| 2016/0088438 | A1* | 3/2016 | O'Keeffe | H01H 9/02 |
| | | | | 455/456.2 |
| 2016/0093412 | A1* | 3/2016 | Liao | A61L 2/10 |
| | | | | 250/221 |
| 2016/0125375 | A1* | 5/2016 | Magee | G07F 19/201 |
| | | | | 705/43 |
| 2016/0323949 | A1* | 11/2016 | Lee | H05B 45/10 |
| 2017/0171949 | A1* | 6/2017 | Kim | H05B 47/11 |
| 2017/0246331 | A1* | 8/2017 | Lloyd | A61L 2/084 |
| 2019/0083809 | A1* | 3/2019 | Zhang | A61N 5/0616 |
| 2019/0192710 | A1* | 6/2019 | Andersson | H05B 47/16 |
| 2019/0289698 | A1* | 9/2019 | Rozendaal | G08C 17/02 |

FOREIGN PATENT DOCUMENTS

| | | | | |
|---|---|---|---|---|
| FR | 3032121 A1 | | 8/2016 | |
| JP | 2009-238454 A | | 10/2009 | |
| WO | WO-2015070006 A1 | * | 5/2015 | ........... A61B 3/0025 |
| WO | 2015168768 A1 | | 11/2015 | |
| WO | WO-2015168768 A1 | * | 11/2015 | ......... H05B 37/0227 |
| WO | 2016049143 A2 | | 3/2016 | |
| WO | 2016070006 A2 | | 5/2016 | |
| WO | 2016070006 A3 | | 5/2016 | |

OTHER PUBLICATIONS

EESR mailed Mar. 15, 2017, pp. 1-8 for EP 16187071 2.
Japanese Office Action 2019-511688.

* cited by examiner

LIGHT CONTROL SYSTEM AND A METHOD FOR EXPOSING A SUB-PORTION OF A SPACE WITH LIGHT WITHIN A PREDETERMINED SPECTRAL RANGE AT A PREDETERMINED THRESHOLD INTENSITY

CROSS-REFERENCE TO RELATED APPLICATION

This Application is the National Stage filing under 35 U.S.C. § 371 of PCT Application Ser. No. PCT/EP2017/071939 filed on Sep. 1, 2017, which claims the benefit of European Patent Application No. 16187071.2 filed on Sep. 2, 2016. The disclosures of both applications are hereby incorporated herein by reference in their entireties.

TECHNICAL FIELD

The present invention relates to a light control system and a method for exposing a sub-portion of a space with light within a predetermined spectral range at a predetermined threshold intensity.

BACKGROUND OF THE INVENTION

Light is crucial for the well-being of humans and animals. With the technical evolution of artificial light, much driven by the development of light emitting diodes, improved light sources are now in the hands of the light designers. The light sources allow, for example, for mimicking of daylight in an indoor environment, but also offer new possibilities to create unique lighting within an environment. The safety of humans or animals must, however, be considered when designing efficient lighting solutions in order to prevent discomfort for or damage to humans or animals. To achieve improved lighting solutions there is also a need for efficient control of the spectral range and/or spatial distribution of artificial light in the space.

SUMMARY OF THE INVENTION

In view of the above, it is an object of the present invention to provide efficient lighting in a space, more particular to efficiently expose a sub-portion of a space with light within a predetermined spectral range at a predetermined threshold intensity.

According to a first aspect a light control system is provided. The light control system comprising: a plurality of light sources each configured to emit light within a predetermined spectral range, each of the plurality of light sources being configured to illuminate a corresponding sub-portion of a space, a sensor configured to within the space, detect a location of a human or an animal; and a control engine configured to control the plurality of light sources based on the detected location of the human or the animal such that a sub-portion of the space in which the human or the animal is not present is exposed to the light within the predetermined spectral range at a predetermined threshold intensity.

Efficient illumination of a sub-portion of a space with light with a predetermined spectral range at the predetermined threshold intensity is thereby provided. The human or the animal is, moreover, prevented from being exposed to the light within the predetermined spectral range at the predetermined threshold intensity.

The availability of a space may further be increased as humans or animals may be present in the space without being exposed to the light within the predetermined spectral range at the predetermined threshold intensity.

An improved usage of the plurality of light sources is further provided, i.e. only light sources pertaining to a sub-portion where no human or animal is present is emitting light. The lifetimes of the light sources may thereby be increased.

The control engine may further be configured to control the plurality of light sources based on the detected location of the human or the animal such that the exposure of the sub-portion of the space to light having the predetermined spectral range at the predetermined threshold intensity is terminated when the human or the animal enters the light exposed sub-portion.

The time the human or the animal is exposed to the light having the predetermined spectral range at the predetermined threshold intensity is thereby efficiently reduced. The amount of light reaching the human or the animal may thereby be reduced. Distressing or harmful light exposure for the human or the animal may thereby be prevented.

The control engine may further be configured to control the plurality of light sources based on the detected location of the human or the animal such that the exposure of the sub-portion of the space to light having the predetermined spectral range at the predetermined threshold intensity is terminated when the human or the animal is within a safety distance from the light exposed sub-portion.

The safety distance may be in the range of 0.5 m to 10 m.

The light having the predetermined spectral range may thereby be terminated prior to the human or animal enters into the illuminated sub-portion. Exposure of light being distressing or harmful for a human or an animal may, for example, be prevented from reaching the human or the animal.

The sensor may further be configured to within the space, detect a spatial distribution of light within the predetermined spectral range.

The sensor may thereby determine which location or locations in the space that comprises the light within the predetermined spectral range. Information pertaining to if a sub-space in the space is illuminated or not with light within the predetermined spectral distribution may thereby be obtained.

The sensor may with spatial resolution determine the amount of light within the predetermined spectral range. The sensor may further determine if a given sub-portion in the space receives light within the predetermined spectral range at the predetermined threshold intensity.

The control engine may further be configured to control the plurality of light sources based on the detected location of the human or the animal and on the spatial distribution of light such that the exposure of the sub-portion of the space to light within the predetermined spectral range is terminated when the human or the animal enters the light exposed sub-portion.

The wording terminated may be construed as that the light exposure of light within the predetermined spectral range at the predetermined threshold intensity is turned off. The wording terminated may alternatively be construed as that the light exposure is reduced in intensity from being at or above the predetermined threshold intensity to being below the predetermined threshold intensity. The exposure may thereby be reduced from the predetermined threshold intensity, which may be harmful to a human or an animal, to a lower intensity, which may not be harmful to the human or the animal. The lower intensity level of light may be referred to as a safety light intensity level.

Each of the plurality of light sources may further be tunable in their light emission of light such that the emitted light may be shifted in spectral range. The predetermined spectral range may thereby be altered to different wavelength ranges. The predetermined spectral range may further be increased or decreased or shifted in wavelength.

The plurality of light sources may further be configured to emit light within an additional predetermined spectral range, the additional predetermined spectral range being different from the predetermined spectral range.

The plurality of light sources may be configured to simultaneously emit light within the predetermined spectral range and the additional predetermined spectral range. The plurality of light sources may thereby, for example, emit multi-color light.

The light within the additional predetermined spectral range may be at another predetermined threshold intensity as compared with the predetermined threshold intensity for the light in the predetermined spectral range.

The light control system may further comprise additional light sources configured to emit light within an additional predetermined spectral range. The The control engine may be configured to control the additional light sources.

The control engine may further be configured to control the plurality of light sources such that the sub-portion of the space being exposed to the light within the predetermined spectral range is additionally exposed to light within the additional predetermined spectral range.

An additional sub-portion of the space, other than the sub-portion being exposed to the light within the predetermined spectral range, may additionally be exposed to the additional predetermined spectral range.

The light of the additional predetermined spectral range may thereby be used to signal to a human or an animal that light within the predetermined spectral range at the predetermined threshold intensity is illuminating a sub-portion of the space.

The sub-portion of a space may be a sub-portion of a room.

The sub-portion of a space may be a room.

At least two of the sub-portions of the space may be overlapping. An increased intensity of the light having a predetermined spectral range may thereby be achieved in the illuminated sub-portions.

At least two of the sub-portions of the space may be non-overlapping. A simpler control of the illumination in a sub-portion of a space may thereby be provided.

The light having the predetermined spectral range may be in the ultraviolet spectral range.

The ultraviolet spectral range may be in the range of UV-C.

Ultraviolet light may kills germs, especially pathogenic microorganisms and thereby provide a disinfecting effect in an illuminated sub-portion of a space. Ultraviolet light thereby provides efficient sterilization of workspaces, equipment and tools which may be used in medical facilities such as hospitals, nursing homes or laboratories such as medical and biological laboratories. Ultraviolet light may also provide efficient sterilization at public or private institutions such as elderly homes, day care centers for children, or schools. Ultraviolet light may further have a disinfecting effect in an illuminated sub-portion of a space. An animal barn or a sub-portion of an animal barn not comprising an animal may alternatively be illuminated with light having the predetermined spectral range at the predetermined threshold intensity.

The wording ultraviolet light may be construed as electromagnetic radiation having a wavelength in the range from about 100 nm to 400 nm, i.e. shorter than visible light. Ultraviolet light may be understood as being part of the light spectrum, and may typically be classified into three wavelength ranges: UV-C, from about 190 nm to 290 nm, UV-B, from about 290 nm to 320 nm, and UV-A, from about 320 nm to 380 nm.

UV-C provides efficient prevention of bacteria. In other words, UV-C light may be germicidal. Germs may be understood as microscopic bacteria, viruses, fungi, and protozoa that may cause disease.

The skilled person in the art realizes that the different ranges discussed above for the ultraviolet range may differ in different literature. UV-C may, for example, also be defined to comprise the wavelength range 100 nm to 300 nm. The ultraviolet light may further comprise vacuum UV defined to be in the range from about 10-190 nm.

The predetermined spectral range may be equal for all the plurality of light sources.

A light source or a plurality of light sources may thereby provide a predetermined dosage of ultraviolet light in a sub-portion of a space. The predetermined dosage may be in the range of 1 000 to 500 0000 microwatt seconds per square centimeter, typically in the range of 10 000 to 20 0000 microwatt seconds per square centimeter or higher. The light source may, for example, provide a light dosage in the range of 30 000 to 50 000 microwatt seconds per square centimeter or higher. The person skilled in the art realizes that the product of time and intensity may be used for providing efficient germicidal illumination.

It should be noted that dosage, which may be referred to as fluence, may be obtained by multiplying the fluence rate, or irradiance, by the exposure time in seconds. Hence, the predetermined threshold intensity may, for example, be understood to be an intensity of light which provides the desired dosage within a predetermined time interval. The predetermined interval may, for example, range from seconds to hours depending on application. Longer exposure times such as over night or for a day may alternatively be used.

The control engine or the sensor may be configured to a determine location coordinate of the human or the animal in the space. The control engine or the sensor thereby allows a human or an animal to be efficiently located in the space. A simplified tracking of the human or the animal in the space may thereby be achieved. The control engine or the control engine and the sensor may, moreover, provide combined spatial mapping of light and presence mapping of the human or animal in the space. A better control of the light distribution in the space may thereby be obtained. The trajectory of the human may further be determined and used to predict a future location of the human or animal, i.e. to predict if a human or animal is approaching or entering a given sub-portion of the space.

The sensor may comprise an image sensor. An image of the space or a sub-portion of the space may thereby be captured. The presence of the human or the animal may, moreover, be detected. The location of the human or animal in the space may further be determined from the captured image. The human or animal may be detected using any known object detection method.

According to a second aspect of the invention a method for exposing a sub-portion of a space with light having a predetermined spectral range at a predetermined threshold intensity is provided. The method comprising: detecting a location of a human or an animal within the space; exposing, based on the detected location of the human or the animal a sub-portion of the space in which the human or the animal is not present with light within the predetermined spectral range at the predetermined threshold intensity by controlling a plurality of light sources arranged in the space, each light source configured to emit light within a predetermined spectral range and configured to illuminate a corresponding sub-portion of the space.

The method may further comprise: detecting a spatial distribution of light within the predetermined spectral range within the space; and wherein the act of exposing is based on the detected location of the human or the animal and the detected spatial distribution of light.

The above mentioned features of the light control system, when applicable, apply to this second aspect as well. In order to avoid undue repetition, reference is made to the above.

A further scope of applicability of the present invention will become apparent from the detailed description given below. However, it should be understood that the detailed description and specific examples, while indicating preferred embodiments of the invention, are given by way of illustration only, since various changes and modifications within the scope of the invention will become apparent to those skilled in the art from this detailed description.

Hence, it is to be understood that this invention is not limited to the particular component parts of the device described or steps of the methods described as such device and method may vary. It is also to be understood that the terminology used herein is for purpose of describing particular embodiments only, and is not intended to be limiting. It must be noted that, as used in the specification and the appended claim, the articles "a," "an," "the," and "said" are intended to mean that there are one or more of the elements unless the context clearly dictates otherwise. Thus, for example, reference to "a unit" or "the unit" may include several devices, and the like. Furthermore, the words "comprising", "including", "containing" and similar wordings do not exclude other elements or steps.

BRIEF DESCRIPTION OF THE DRAWINGS

The above and other aspects of the present invention will now be described in more detail, with reference to appended drawings showing embodiments of the invention. The figures should not be considered limiting the invention to the specific embodiment; instead they are used for explaining and understanding the invention.

As illustrated in the figures, the sizes of layers and regions are exaggerated for illustrative purposes and, thus, are provided to illustrate the general structures of embodiments of the present invention. Like reference numerals refer to like elements throughout.

DETAILED DESCRIPTION

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and to fully convey the scope of the invention to the skilled person.

In the following a light control system and a method for exposing a sub-portion of a space with light within a predetermined spectral range is described in relation to FIGS. 1-4.

Figure 1A:
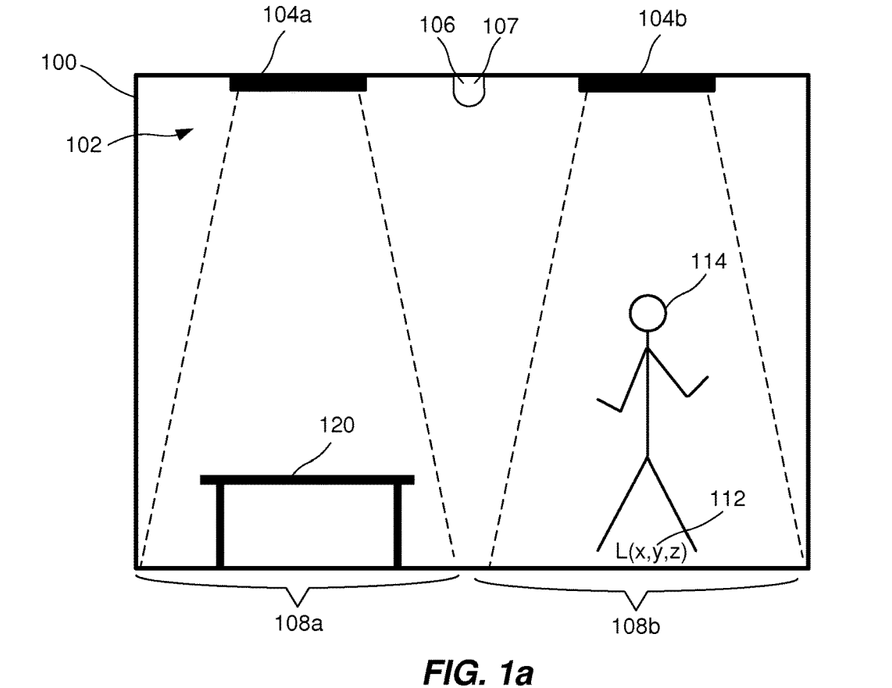
FIGS. 1a and 1b illustrate schematic views of a space comprising a light control system.
Figure 1B:
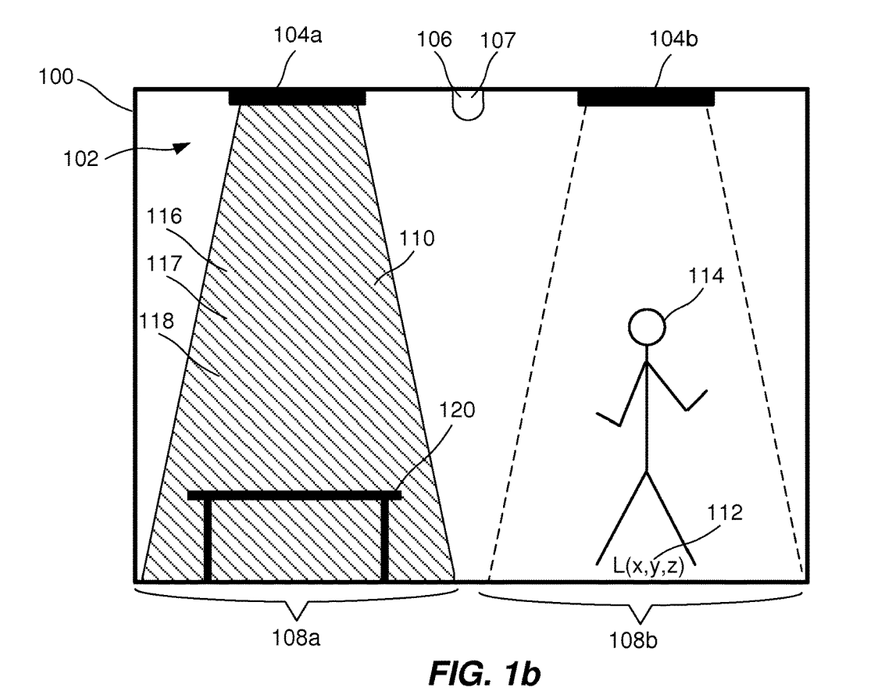
Figure 4:
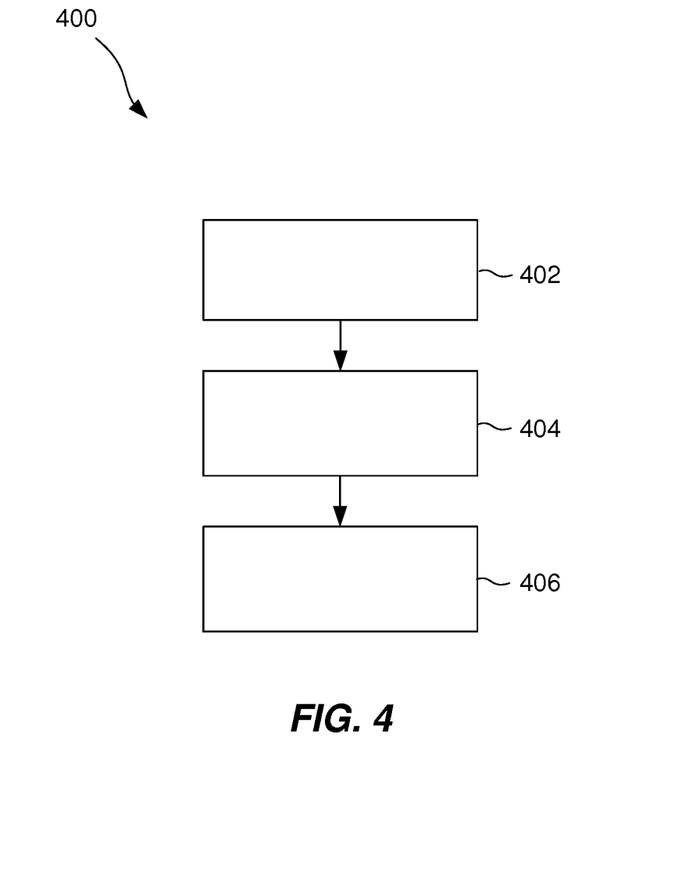
FIG. 4 illustrates a block diagram of a method for exposing a sub-portion of a space with light within a predetermined spectral range at a predetermined threshold intensity.

FIGS. 1a and 1b illustrate schematic views of a space 100 comprising a light control system 102. FIG. 4 illustrates a block diagram of a method 400 for exposing a sub-portion of a space with light within a predetermined spectral range at a predetermined threshold intensity.

The space 100 is illustrated as a room, but may, for example, be a building such as a hospital, a nursing home or a school.

The light control system 102 comprises a plurality of light sources 104, illustrated by two light sources 104a, 104b, a sensor 106 and a control engine 107. The control engine 107 is illustrated as being comprised in the sensor 106, but may be physically separate from the sensor 106.

The control engine may form or be implemented in a separate unit in the space 100.

The control engine may alternatively be implemented on a remote server or on a central server or as part of a cloud service.

The control engine and the sensor may communicate with each other over a wired or wireless communication network. The control engine 107 may be comprised in a single device. Alternatively, the control engine 107 may be distributed over a plurality of devices.

The light sources 104 may be solid state based light sources, e.g. light based on LED-, OLED-, AMOLED-, Electro Luminescent wire-, or LASER-technology. The light sources may form part of a light panel comprising at least a portion of the plurality of light sources.

The light panel may, for example, comprise different light sources, each emitting light with a certain spectral range. One or several of the light sources within the light panel may emit visible light, ultra-violet light or infra-red light.

Several light panels may be arranged in the space.

Each of the plurality of light sources 104 is configured to emit light within a predetermined spectral range, as will be discussed further below, and to illuminate a corresponding sub-portion 108 of the space 100, illustrated by the sub-portions 108a, 108b in FIG. 1a. More specifically, the light source 104a is configured to illuminate the sub-portion 108a with light within a predetermined spectral range. The light source 104b is configured to illuminate the sub-portion 108b with light having a predetermined spectral range. The two sub-portions 108a and 108b are non-overlapping. A simpler control of the illumination in the space 100 may thereby be provided.

The sensor 106 may be configured to within the space 100 detect 402, see the block diagram of FIG. 4, a spatial distribution of light 110 within the predetermined spectral range, see FIG. 1b. The sensor 106 may further be configured to within the space 100 detect 404 a location 112 of a human 114. The location of the human 114 is exemplified to be within the sub-portion 108b of the space 100. The control engine 107 or the sensor 106 may be configured to determine a location coordinate, L(x,y,z), of the human 114 in the space 100. The location coordinate may comprise data pertaining one, two or three spatial coordinates. The control engine 107 may further be configured to assign a time and/or a date at which the location coordinate is determined.

The location coordinate may comprise data pertaining to geopositioning data.

The sensor 106 may comprise an image sensor whereby the location 112 of the human 114 may be determined by acquiring an image. The image may be used to determine the spatial distribution of light within the predetermined spectral range. The sensor 106 may be a camera configured to capture images or sequences of images such as a video stream. The trajectory of the human 114 may further be determined from the captured images, not shown.

Again referring to FIG. 1b, the control engine 107 is configured to control the plurality of light sources 104a, 104b based on the detected location 112 of the human 114 such that a sub-portion 108a of the space in which the human 114 is not present is exposed 116, to the light 118 within the predetermined spectral range at the predetermined threshold intensity, see also the act 406 of the method 400 in FIG. 4. Hence, light 118 within the predetermined spectral range is not illuminating the sub-portion 108b in which the human 114 is located. The human 114 is thereby prevented from being exposed 116 to light 118 within the predetermined spectral range at the predetermined threshold intensity.

The control engine 107 may further be configured to control the plurality of light sources 104 based on the detected location 112 of the human 114 and on the spatial distribution of light 110 such that the exposure 116 of the sub-portion 108b of the space 100 to light 118 within the predetermined spectral range is terminated when the human 114 enters the light exposed sub-portion, not shown. The control engine may thereby correlate the location of the human and the location or locations in space where light within the predetermined spectral range is present. An improved safety control is thereby provided.

The control engine 107 may communicate with the light sources through a radio frequency band through the use of different radio frequency technologies. Examples of such technologies are Wi-Fi, Bluetooth, W-CDMA, GSM, UTRAN, LTE and NMT. The communication may additionally or alternatively occur via a wired interface.

The light 118 within the predetermined spectral range may be in the ultraviolet, UV spectral range. The ultraviolet light at the predetermined threshold intensity may kill or hinder reproduction of germs, especially pathogenic microorganisms and thereby provide a disinfecting effect in an illuminated sub-portion 108a. A work space 120 within the sub-portion 108a may thereby be illuminated mitigating the presence or growth of, for example, germs on the workspace 120. A cleaner environment in the space 100 may thereby be provided.

The ultraviolet spectral range may be in the range of UV-C. UV-C provides efficient prevention of bacteria. In other words, UV-C light may be germicidal. UV-C may deactivate the DNA of bacteria, viruses and other pathogens and thereby destroys their ability to multiply and cause disease. Specifically, UV-C light causes damage to the nucleic acid of microorganisms by forming covalent bonds between certain adjacent bases in the DNA.

The control engine 107 may further be configured to control the plurality of light sources 104a, 104b such that the sub-portion 108a of the space 100 being exposed 116 to the light within the predetermined spectral range is additionally exposed 117 to light within an additional predetermined spectral range. The additional spectral range is different than the predetermined spectral range. The additional spectral range may, for example, be in the visible range of the light spectrum. The human 114 in the space 100 may thereby, by observing the light within the additional spectral range, be made aware of the light exposure 116 in an efficient way. In other words, the exposure 117 with light within the additional spectral range provides a visual light boundary surrounding the exposed 116 sub-portion 108a preventing a human to enter into the sub-portion 108a. The light within an additional predetermined spectral range may thereby function as an alarm or alert light. The alarm or alert light may have a predetermined color, e.g. red or blue light.

The predetermined spectral range may in a non-limiting example, be in the ultraviolet range and the additional spectral range may be in the blue spectral range of the visible spectrum.

An additional sub-portion of the space, other than the sub-portion being exposed to the light within the predetermined spectral range, may additionally be exposed the additional predetermined spectral range. A larger visual light boundary may thereby be used.

The light of the additional predetermined spectral range may thereby indicate that light within the predetermined spectral range is illuminating a sub-portion of the space.

Figure 2A:
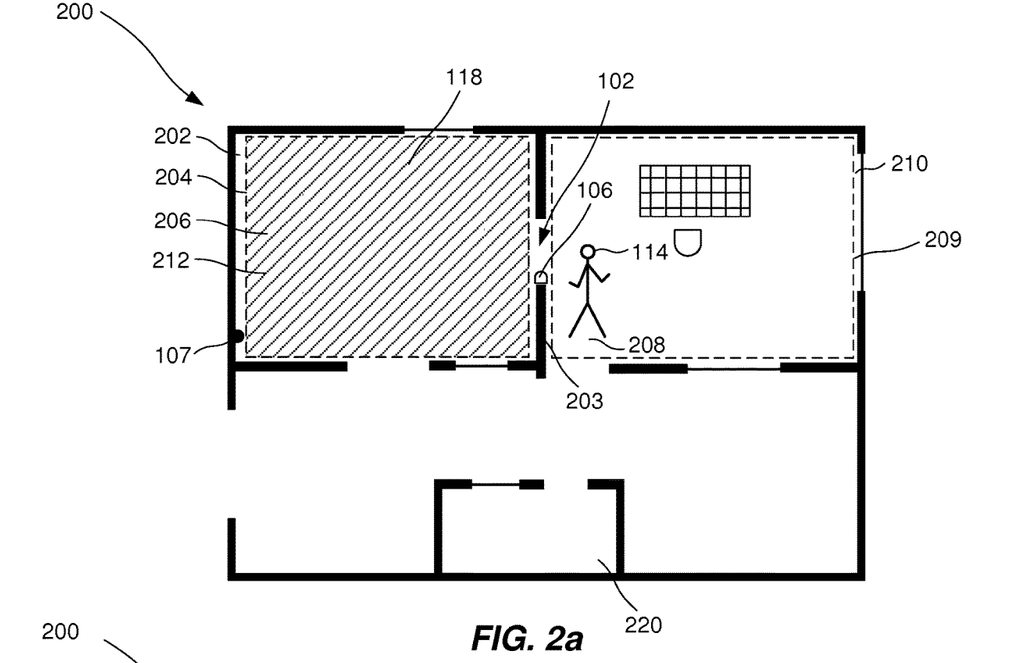
FIGS. 2a and 2b illustrate schematic views of a space comprising a light control system.
Figure 2B:
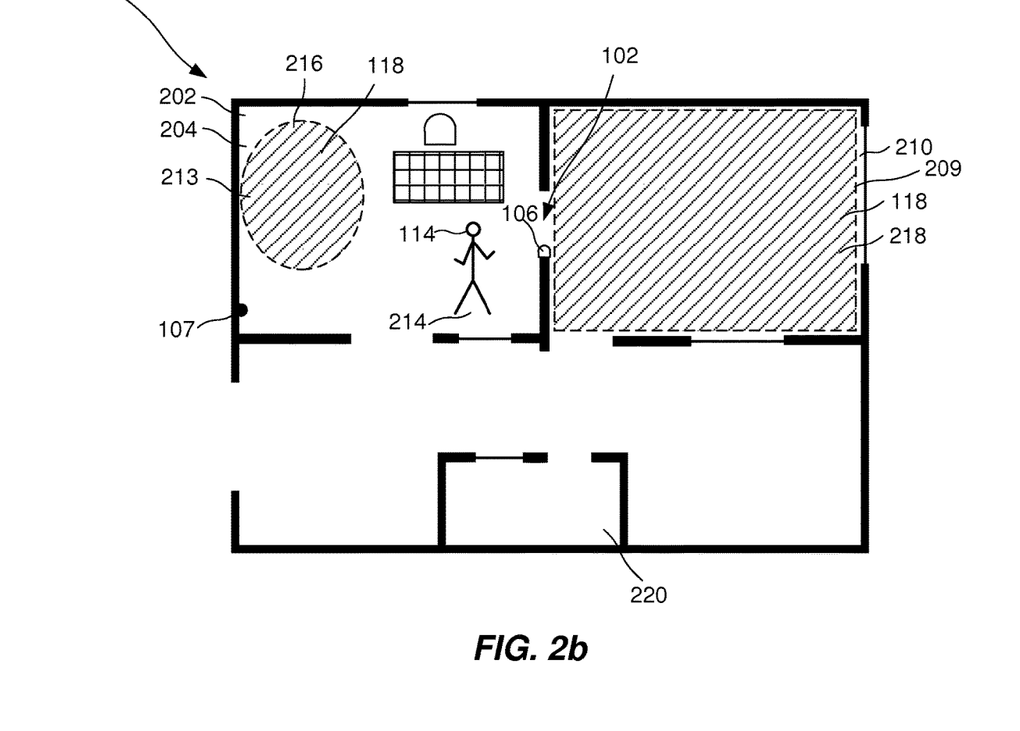

FIGS. 2a and 2b show schematic views of the interior of a house 200, i.e. a space, comprising a light control system 102. A room 202 of the house 200 forms a first sub-portion 204 of the space. The light control system 102 comprises a plurality of light sources, not shown. The light sources may be the light sources 104 described above. Each of the light sources is configured to emit light within a predetermined spectral range, and to illuminate a corresponding sub-portion of a space. The first sub-portion 204, may thereby be illuminated with light 118 within the predetermined spectral range at a predetermined threshold intensity.

The light control system 102 further comprises a sensor 106 and a control engine 107. The control engine 107 is illustrated as being physically separate from the sensor 106. The control engine 107 and the sensor 106 are in communication with each other allowing for transfer of information between the two. The sensor 106 may, for example, be arranged on a wall 203 of the house 200 or in the ceiling of the house 200.

The sensor 106 may be configured to within the house 200, detect a spatial distribution 206 of light 118 within the predetermined spectral range. The sensor 106 may thereby determine a location or locations in the house which are illuminated by light within the predetermined spectral range.

The sensor 106 may further, within the house 200, detect a location 208 of a human 114. In FIG. 2a the spatial distribution 206 of light 118 within the predetermined spectral range at the predetermined threshold intensity is detected to be in room 202. The location 208 of the human 114 is further detected to be in a second sub-portion 209 of the space, i.e. at a location 208 in the room 210 neighboring to the room 202. The control engine 107 may further determine that the location of the human 114 is not within a sub-portion of the space which is exposed to light 118 within the predetermined spectral range. The control engine 107 may further be configured to control the plurality of light sources in the house 200 based on the detected location 208 of the human 114 and on the spatial distribution 206 of light. The room 202 of the house 200, in which the human 114 is not present, may therefore be exposed 212 to the light 118 within the predetermined spectral range at the predetermined threshold intensity. The room 210 in which the human is present is, however, not exposed to light within the predetermined spectral range at the predetermined threshold intensity. Hence, light 118 with the predetermined spectral range is emitted from the light sources such that the human 114 is not exposed to the light 118 at the predetermined threshold intensity.

The control engine 107 may further be configured to control the plurality of light sources based on the detected location 208 of the human 114 such that the exposure 212 of the room 202 to light 118 within the predetermined spectral range is terminated when the human 114 enters the light exposed room 202. This is exemplified in FIG. 2b in which the light exposure 212, of FIG. 2a, is terminated when the human 114 enters into the room 202, i.e. into the first sub-portion 204. In other words, when the human 114 is detected to be at another location 214 within the room 202 the light exposure 212 is terminated. Distressing or harmful light exposure 212 to the human 114 may thereby be prevented.

The control engine 107 may be arranged to expose another sub-portion 216 of the room 202 to light 118 within the predetermined spectral range at the predetermined threshold intensity. Thus a portion 216 of the room 202, in which the human 114 is not present, may be exposed 212 to the light 118. The another sub-portion 216 may, for example, comprise a workspace, sanitary equipment or a kitchen sink.

The control engine 107 may further be arranged to, as the human 114 leaves the room 210, expose 218 the second sub-portion 209 of the room 210 to light 118 within the predetermined spectral range at the predetermined threshold intensity. Distressing or harmful light exposure 118 to the human 114 may thereby be prevented.

The control engine 107 may further be arranged to control the light sources such that a single or a plurality of sub-portions of a space is exposed to light within a predetermined spectral range when no human or animal is present in those sub-portions. Thus, the sub-portions 204, 209 and/or 216 may be exposed to light 118 within the predetermined spectral range at the predetermined threshold intensity, when the human 114, for example, leaves the house 200. The sub-portions 204, 209 and/or 216 may alternatively be exposed to light 118 within the predetermined spectral range at the predetermined threshold intensity, when the human 114 enters into the room 220, see FIGS. 2a and 2b.

It may be noted that at least two of the sub-portions of the space may be overlapping. The sub-portions 204 and 216 are, for example, overlapping. An increased intensity of the light within a predetermined spectral range may thereby be achieved in the illuminated sub-portions such that the predetermined threshold intensity may be reached. To this end, the predetermined spectral range may be equal for all the plurality of light sources. The plurality of light sources may thereby provide a predetermined dosage of light in a sub-portion of a space. The predetermined dosage may be reached by setting a time and an intensity of the light within the predetermined spectral range. The predetermined threshold intensity may be provided by light emitted from a plurality of light sources.

The predetermined spectral range may be different in spectral range for different sub-portions of a space.

The spectral distribution of light within the predetermined spectral range may be the same or be different for different sup-portions of a space.

Figure 3A:
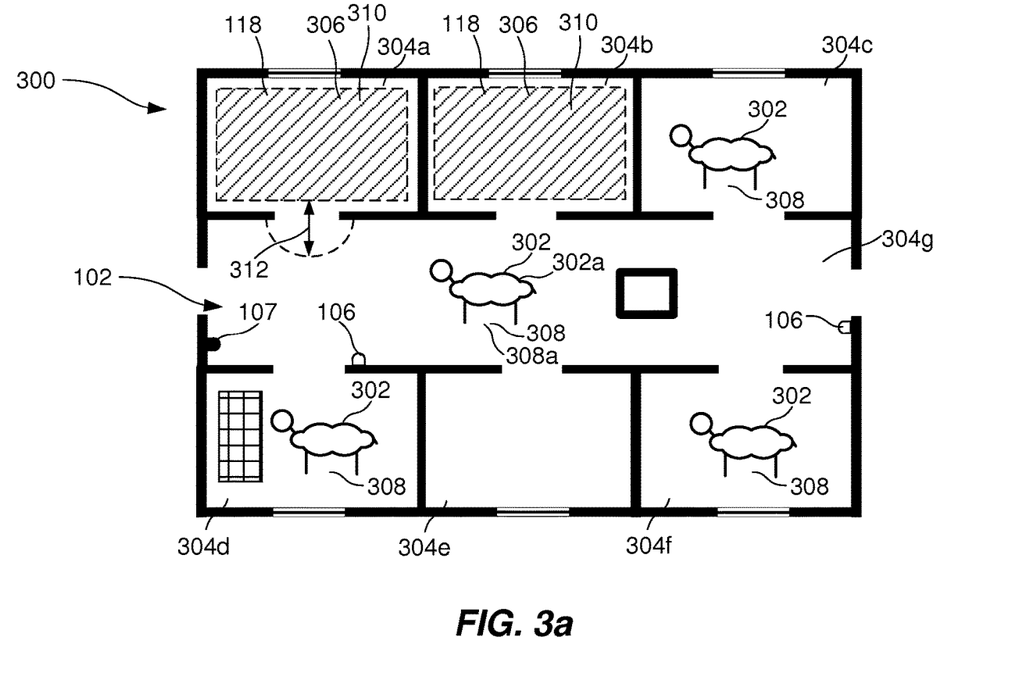
FIGS. 3a and 3b illustrate schematic views of a space comprising a light control system.
Figure 3B:
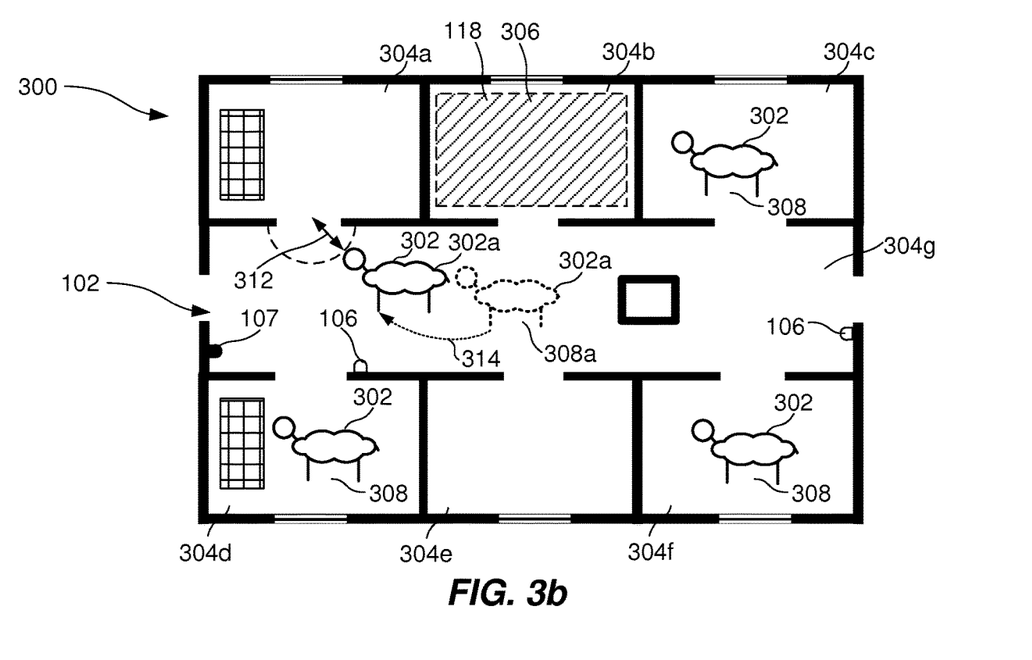

FIGS. 3a and 3b illustrate schematic views of the interior of a space 300. The space 300 is exemplified as a barn 300, comprising animals 302. The space 300 comprises a light control system 102 as described above. The barn 300 is divided into a plurality of sub-portions 304a-304g. The light control system 102 comprises a plurality of light sources, not shown, a plurality of sensors 106 and a control engine 107. The light sources may be the light sources 104 described above. The control engine 107 and the sensors 106 may also be configured as described above. Each of the light sources is configured to emit light 118 within a predetermined spectral range, and to illuminate a corresponding sub-portion 304a-304g of the space 300. The sub-portions 304a and 304b of the barn 300 may thereby be illuminated with light 118 within the predetermined spectral range at the predetermined threshold intensity.

The sensor 106 may be configured to within the barn 300, detect a spatial distribution 306 of light 118 within the predetermined spectral range. The sensor may be configured to within the space 300, detect locations 308 of the animals 302. The control engine 107 is configured to control the plurality of light sources in the barn 300 based on the detected locations 308 of the animals 302 and on the spatial distribution 306 of the light. As exemplified in FIG. 3a, the spatial distribution 306 of light 118 within the predetermined spectral range is detected to be in sub-portions 304a and 304b, whereas the locations 308 of the animals 302 are detected to be in sub-portions 304c, 304d, 304f and 304g of the barn 300. The sub-portion 304a and 304b of the barn 300 may therefore be exposed 310 to the light 118 within the predetermined spectral range at the predetermined threshold intensity. The light exposure 310 may, for example, comprise UV-light having a disinfecting effect on the exposed sections 304a and 304b. The predetermined threshold intensity may further, by the method 400, be set to an intensity level which provides effective disinfection, but which would be distracting or damaging to the animals 302 if the animals 302 were exposed.

At least the sub-portions 304c, 304d, 304f and 304g of the barn 300, in which the animals are present are, however, not exposed to light 118 within the predetermined spectral range at the predetermined threshold intensity.

The sub-portion 304e is in this example not exposed to light 118. The sub-portion 304e may, however, also be exposed to light 118 within the predetermined spectral range at the predetermined threshold intensity as no animal is detected there.

The control engine 107 may further be configured to control the plurality of light sources based on the detected locations 308 of the animals 302 such that the exposure of a sub-portion 304a of the space 300 to light 118 within the predetermined spectral range within the predetermined spectral range at the predetermined threshold intensity is terminated when an animal 302a is within a safety distance 312 from a light exposed sub-portion 304a. The safety distance 312 may, for example, be in the range of 0.5 m to 10 m. The safety distance 312 may alternatively be larger or smaller, depending on, for example, the dimensions of the space and/or the sensitivity of a human or animal for being exposed to the light within the predetermined spectral range.

More specifically, the animal 302a is in FIG. 3a illustrated to be located within the sub-portion 304g. For the location 308a of the animal 302a it is safe to, for example, expose 310 the sub-portions 304a and 304b to light 118. As the animal 302a, however, moves 314 towards the sub-portion 304a and reaches the safety distance 312 from the sub-portion 304a, the light 118 exposure is terminated, compare FIGS. 3a and 3b. The light 118 within the predetermined spectral range at the predetermined threshold intensity may thereby be terminated prior to the animal 302a enters into sub-portion 304a. Light exposure of the animal 302a which may be distressing or harmful for the animal 302 may thereby be prevented.

The light exposure may alternatively be reduced in intensity from being at or above the predetermined threshold intensity to being below the predetermined threshold intensity when an animal 302 enters into a sub-portion 304a being exposed to the light within the predetermined spectral range. The light exposure may thereby be reduced from the predetermined threshold intensity, which may be harmful to the animal, to a lower intensity, which may not be harmful to the human or the animal.

In the above the detection and prevention of light exposure of a human or an animal in the space have been discussed. Alternatively or in combination the detection may be of a human and an animal and the prevention of light exposure may relate to the detected human and/or animal.

The light within the predetermined spectral range described above may be in the ultraviolet spectral range. The ultraviolet spectral range may be in the range of UV-C. Ultraviolet light is used to disinfect and sterilize, for example, surfaces, workspaces, equipment and tools used in laboratories, medical facilities, as well as in kitchens, bathrooms and animal barns. Light sources such as light emitting diodes, lasers and low-pressure mercury-vapor lamps may emit light in the ultra violet spectral range. Ultraviolet light at, for instance, 254 nm may damage a microorganism's DNA so that it cannot reproduce, making it less harmful for a human or animal.

Catalytic chemical reactions from for instance titanium dioxide and UV-C light UV-C, exposure, i.e. light exposure with light having a wavelength from about 190 nm to 290 nm, may further induce oxidation of organic matter converting pathogens, pollens, and mold spores into harmless inert by-products. The cleansing mechanism of UV may thereby be understood as is a photochemical process. Contaminants in the indoor environment are almost entirely organic carbon-based compounds, may thereby break down when exposed to ultraviolet light at 240 nm to 280 nm.

The light within the predetermined spectral range described above may alternatively be in the visible, about 380 nm to 750 nm, and or the infra-red spectral range, about 750 nm to 1 mm, of light. Light exposure of a human or animal to light at these wavelengths may be prevented. Thus, light exposure of a human or an animal with light having a color, a range of colors or an intensity level which is/are disturbing or harming to a human or animal may be avoided. The exposure form infra-red light sources may further be reduced. Heating of a human or animal which may be associated with the light exposure of infra-red light at a predetermined threshold intensity may thereby be mitigated.

As a non-limiting example, premature infants are sensitive to light exposure. Infants born before the 37th week of gestation are considered born prematurely. Premature infants are not fully developed. For example, the type and intensity of visual stimuli may affect the development of visual acuity and color vision. Furthermore, the retinal vasculature of premature infant eyes is developing and may therefore be easily damaged by light exposure. To this end, light or other visual stimuli may stress the bodies of the premature infants. Thus, a nurse will normally cover the incubator of the premature infant. Alternatively, and/or in combination the neonatal intensive care unit, NICU, in which the premature baby is located may dim the lights at night to prevent exposure of light to the premature infant. This management of light, however, requires additional work.

It is therefore advantageous to allow for light exposure in a sub-portion of a space in which the premature infant is not present while preventing light exposure in a sub-space where the infant in present. More specifically, a light control system, as described above, may be provided. The light control system may comprise a plurality of light sources each configured to emit light within a predetermined spectral range. Each of the plurality of light sources may be configured to illuminate a corresponding sub-portion of a space. The light control system may further comprise an image sensor. The image sensor may be arranged to acquire one or more images. and the light control system may further comprise a control engine. The control engine may be configured to; using an image acquired by the image sensor, detect, within the space, a spatial distribution of light within the predetermined spectral range. The control engine may further be configured to use an image acquired by the image sensor, to determine a location coordinate of a premature infant in the space. The control engine may further be configured to control the plurality of light sources based on the location coordinate of the premature infant and on the spatial distribution of light. This such that a sub-portion of the space in which the premature infant is not present is exposed to the light within the predetermined spectral range at a predetermined threshold intensity. Hence, the NICU may be illuminated with ordinary "daylight" light while the sub-portion wherein the premature infant is present will not be illuminated with light that is harmful or causing discomfort to the premature infant.

According to one example, the light within the predetermined spectral range may be visible light below a wavelength of 600 nm. Thus, light in a wavelength range below 600 nm may be used for illuminating sub-portions in the space in which the premature infant is not present and at the same time the premature infant is protected from visible light having a wavelength below 600 nm. According to another example the light within the predetermined spectral range may be visible light below a wavelength of 500 nm. Thus, light in a wavelength range below 500 nm may be used for illuminating sub-portions in the space in which the premature infant is not present and at the same time the premature infant is protected from visible light having a wavelength below 500 nm. This allow for protecting the premature infant from harmful light while maintaining a suitable work environment at the NICU.

The control engine may be configured to, using an image acquired by the image sensor, determine a location coordinate of a premature infant in the space. The control engine may further, using an image acquired by the image sensor, differentiate between a premature infant and other humans in the space. The control system may use a relative height and/or width of objects within the acquired image or images to differentiate between a premature infant and other humans in the space. Personnel and/or parents to the premature infants may thereby be exposed to normal "daylight", hence light within the whole visible spectrum, while the premature infant is protected from light that might be harmful for the premature infant. This management of light reduces the need for additional work such as covering up the premature infants for light exposure and may further lead to more favorable lighting conditions around the premature infants. Thus, light for visual guidance and for providing reading light for the personnel and visitors of the NICU may be achieved.

The above discussion regarding premature infants also holds for prematurely born animals which also may be sensitive to light exposure within a predetermined spectral range.

The person skilled in the art realizes that the present invention by no means is limited to the preferred embodiments described above. On the contrary, many modifications and variations are possible within the scope of the appended claims.

For example, the space may be an outdoor or an indoor space.

It should be noted that the light source may be a light fixture mounted, for example, in a ceiling or be a spot light source arranged in the space.

The control engine may be software and/or hardware implemented. For example, the control engine may be implemented by a processor running executable computer program instructions. The processor may be a general-purpose or special-purpose processor. The executable computer program instructions may be stored on the memory. Hence, the processor is configured to read instructions from the memory and execute these instructions to control the operation of the light control system.

The memory may be implemented using any commonly known technology for computer-readable memories, such as ROM, RAM, SRAM, DRAM, CMOS, FLASH, DDR, SDRAM or some other memory technology. The memory may also be arranged to store information be processed by the control engine. The memory may be configured to store at least parts of the database.

The sensor may comprise an image sensor and the sensor and/or the control engine may be configured to make a distinction between a human and an animal or between different animals. The predetermined spectral range and or the predetermined threshold intensity may be dependent on if a human or an animal is detected and what type of animal it is.

The intensity of the light exposure of a sub-portion may further be based on if a human or an animal is detected outside the light exposed sub-portion. The intensity of the light exposure may, for example be larger if no human is detected outside the sub-portion of the space.

The safety distance may, moreover, be based on if a human or animal is detected outside the light exposed sub-portion. The safety distance may be larger for a human than for an animal.

Additionally, variations to the disclosed embodiments can be understood and effected by the skilled person in practicing the claimed invention, from a study of the drawings, the disclosure, and the appended claims.

What is claimed is:

1. A light control system comprising:
    a plurality of light sources each configured to emit light within a predetermined spectral range 190 nm to 290 nm in a UV-C range of ultraviolet light, each of the plurality of light sources being configured to illuminate a corresponding sub-portion of a space with light within the predetermined spectral range in the UV-C range,
    an image sensor arranged to acquire one or more images; and
    a control engine configured to;
    using an image acquired by the image sensor, detect, within the space, a spatial distribution of light within the predetermined spectral range in the UV-C range,
    using an image acquired by the image sensor, determine a location coordinate of a human or an animal in the space, and
    control the plurality of light sources based on the location coordinate of the human or the animal and on the spatial distribution of light, such that a sub-portion of the space in which the human or the animal is not present is exposed to the light within the predetermined spectral range in the UV-C range at a predetermined threshold intensity, and such that the exposure of the sub-portion of the space to light within the predetermined spectral range in the UV-C range is reduced in intensity from being at the predetermined threshold intensity to being below the predetermined threshold intensity when the human or the animal enters the light exposed sub-portion.

2. The light control system according to claim 1, wherein the control engine is further configured to control the plurality of light sources based on the detected location of the human or the animal such that the exposure of the sub-portion of the space to light within the predetermined spectral range in the UV-C range at the predetermined threshold intensity is terminated when the human or the animal is within a safety distance from the light exposed sub-portion (304a).

3. The light control system according to claim 2, wherein the safety distance is in the range of 0.5 m to 10 m.

4. The light control system according to claim 1, wherein the control engine is further configured to control the plurality of light sources based on the detected location of the human or the animal and on the spatial distribution of light such that the exposure of the sub-portion of the space to light within the predetermined spectral range in the UV-C range is terminated when the human or the animal enters the light exposed sub-portion.

5. The light control system according to claim 1, wherein at least two of the sub-portions of the space are overlapping.

6. The light control system according to claim 1, wherein at least two of the sub-portions of the space are non-overlapping.

7. The light control system according to claim 1, wherein the predetermined spectral range in the UV-C range is equal for all the plurality of light sources.

8. The light control system according to claim 1, wherein the control engine or the sensor is configured to determine a location coordinate of the human or the animal in the space.

9. A method for exposing a sub-portion of a space with light within a predetermined spectral range 190 nm to 290 nm in a UV-C range at a predetermined threshold intensity, the method comprising:
    acquiring one or more images of the space;
    based on an acquired image, detecting a location coordinate of a human or an animal within the space;
    based on an acquired image, detecting a spatial distribution of light within the predetermined spectral range in the UV-C range within the space;
    exposing, based on the detected location coordinate of the human or animal, and on the detected spatial distribution of light within the predetermined spectral range in the UV-C range within the space, a sub-portion of the space in which the human or animal is not present with light within the predetermined spectral range in the UV-C range at the predetermined threshold intensity by controlling a plurality of light sources arranged in the space, each light source configured to emit light within a predetermined spectral range and configured to illuminate a corresponding sub-portion of the space with light within the predetermined spectral range in the UV-C range, wherein the exposure of the sub-portion of the space to light within the predetermined spectral range in the UV-C range is reduced in intensity from being at the predetermined threshold intensity to being below the predetermined threshold intensity when the human or the animal enters the light exposed sub-portion.

* * * * *